United States Patent [19]

Chen

[11] Patent Number: 5,360,018
[45] Date of Patent: Nov. 1, 1994

[54] POSITIONABLE VIEWING SHIELD WITH DISPOSABLE TRANSPARENT MEDIUM

[76] Inventor: Sutton Chen, 7866 East Roseland Dr., La Jolla, Calif. 92037

[21] Appl. No.: 154,395

[22] Filed: Nov. 18, 1993

Related U.S. Application Data

[63] Continuation of Ser. No. 887,889, May 26, 1992, abandoned.

[51] Int. Cl.$^5$ .................... A61B 19/00; A61F 5/37
[52] U.S. Cl. .................... 128/849; 128/846; 128/863; 128/917
[58] Field of Search ................ 128/846, 849, 851, 863, 847, 917; 359/894, 811, 812, 818, 827; 141/97; 38/102.0, 102.1, 102.2, 102.91; 106/380; 248/121, 122, 125, 106

[56] References Cited

U.S. PATENT DOCUMENTS

| | | | |
|---|---|---|---|
| 1,249,057 | 12/1917 | Finley | 38/102.2 |
| 1,480,298 | 1/1924 | Pearson | 160/380 |
| 2,597,670 | 5/1952 | Pinto | 248/122 X |
| 2,628,803 | 2/1953 | Krewson | 128/849 X |
| 2,641,965 | 6/1953 | Valenza | 359/818 X |
| 2,861,501 | 11/1958 | Strelakos | 359/811 X |
| 3,428,286 | 2/1969 | Del Pesco | 359/811 X |
| 3,537,447 | 11/1970 | Gauthier et al. | 128/139 |
| 3,575,407 | 4/1971 | Carson | 128/849 X |
| 3,750,312 | 8/1973 | Bucher | 38/102.2 |
| 3,871,752 | 3/1975 | Habinger | 359/818 X |
| 4,082,092 | 4/1978 | Foster | 128/139 |
| 4,175,343 | 11/1979 | Mathews | 38/102.1 |
| 4,275,719 | 6/1981 | Mayer | 128/847 |
| 4,422,250 | 12/1983 | Golan | 38/102.2 |
| 4,485,853 | 12/1984 | Gunderson | 141/1 |
| 4,590,695 | 5/1980 | McGilliuray | 38/102.2 |
| 4,644,639 | 2/1987 | Atteberry et al. | 38/102.2 X |
| 4,653,715 | 3/1987 | Schmidt et al. | 248/122 X |
| 4,936,318 | 6/1990 | Schoolman | 128/847 |
| 4,998,538 | 12/1991 | Charowsky et al. | 128/856 |
| 5,033,170 | 7/1991 | Ewert | 24/459 |

FOREIGN PATENT DOCUMENTS

| | | | |
|---|---|---|---|
| 0366618 | 5/1990 | European Pat. Off. | 128/849 |
| 2614292 | 10/1977 | Germany | 128/849 |
| 446669 | 4/1935 | United Kingdom . | |

Primary Examiner—Robert A. Hafer
Assistant Examiner—Brian E. Hanlon
Attorney, Agent, or Firm—Charles J. Prescott

[57] ABSTRACT

A viewing device which includes a support; a splash guard with a peripheral wall enclosing an open area to permit visual observation therethrough, with the wall having a surface thereon to receive and support a disposable transparent film positioned across said open area; a post for positioning the splash guard; and a releasable restraint cooperating with the wall surface to releasably secure the transparent film positioned under tension across the open viewing area. There are also adjusting components to permit the splash guard to be positioned in varying angular orientations and at varying heights relative to the support. A variety of restraints are suitable, including resilient bands, toggle straps, flanged caps and compression springs. The device may be used with a variety of transparent films, polyethylene, polypropylene, cellulose acetate, polyester, polyvinylidene chloride and polysulfone. The device is most valuable in medical emergency room use, but it can also be used in a variety of other settings, including operating rooms, for out-patient examination, in individual physicians' offices, by veterinarians and for inspection or repair of small mechanical products where lubricants, cleaners or other liquids used with such products might be sprayed or splashed into the user's face.

16 Claims, 3 Drawing Sheets

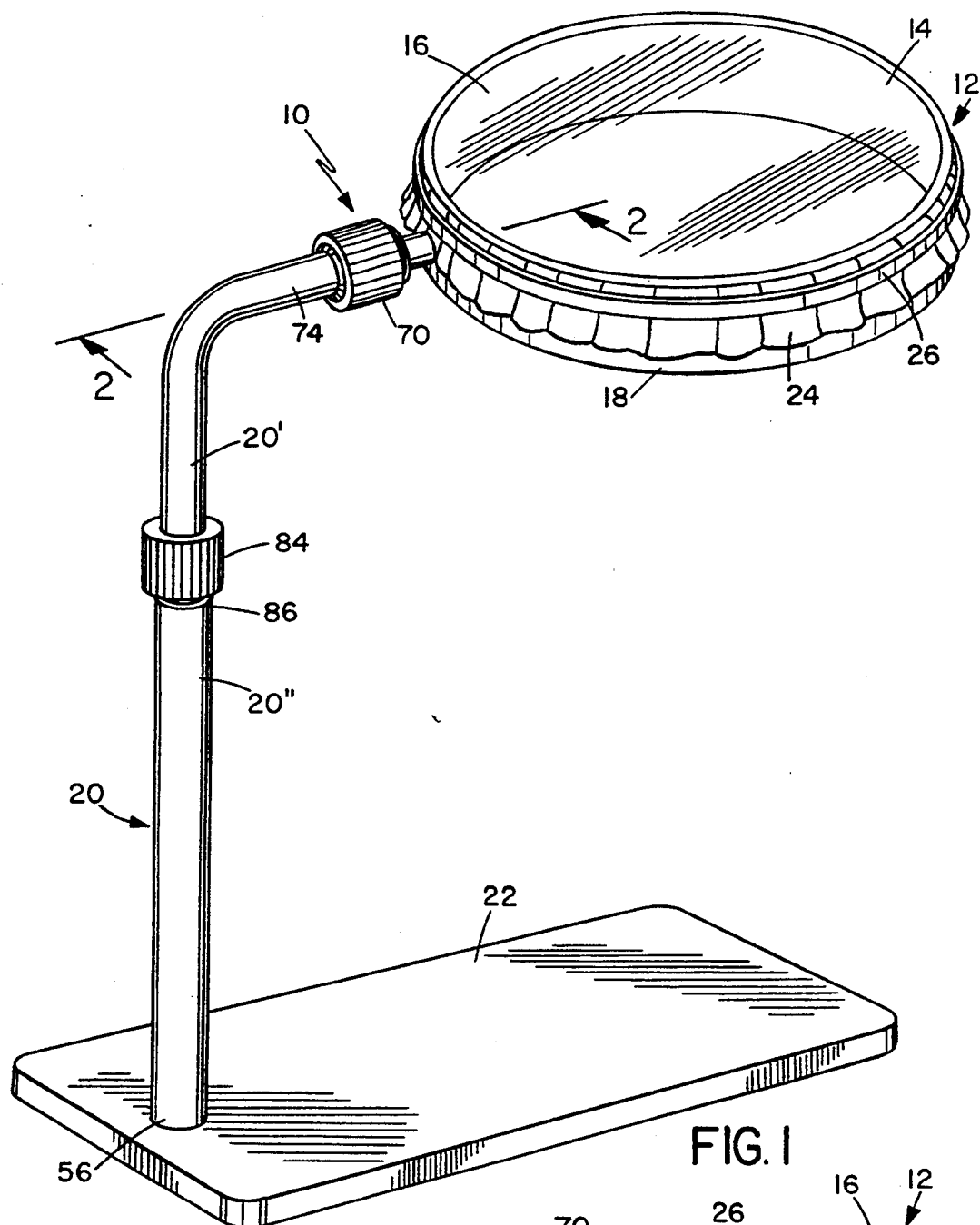
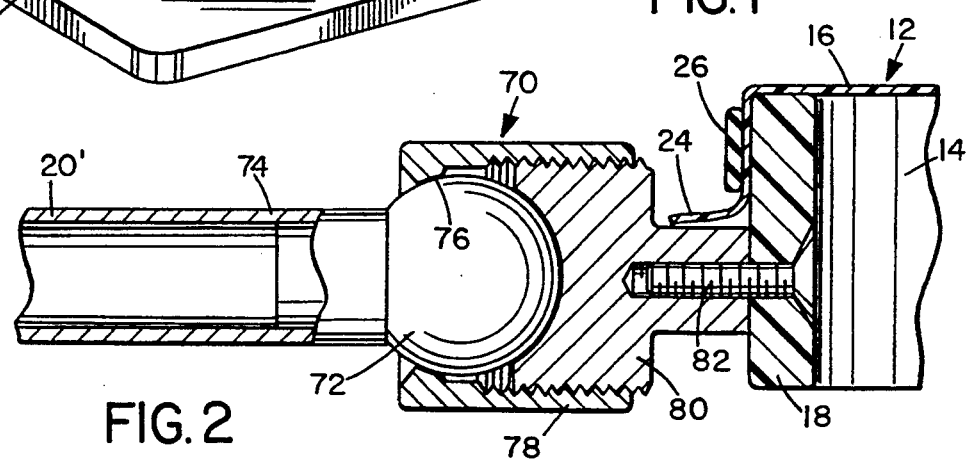

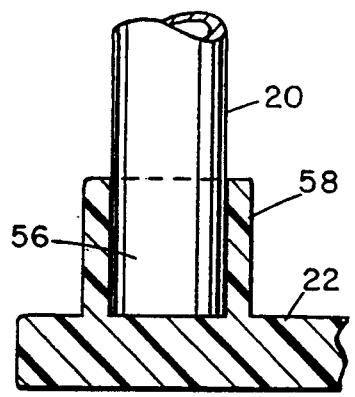
FIG. 6
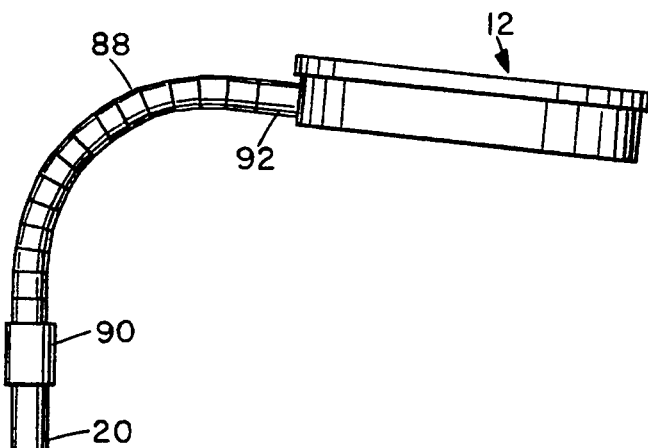
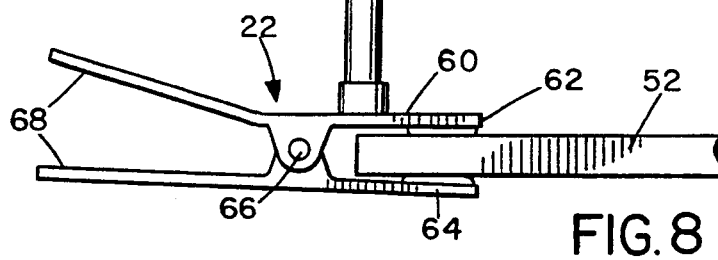
FIG. 8
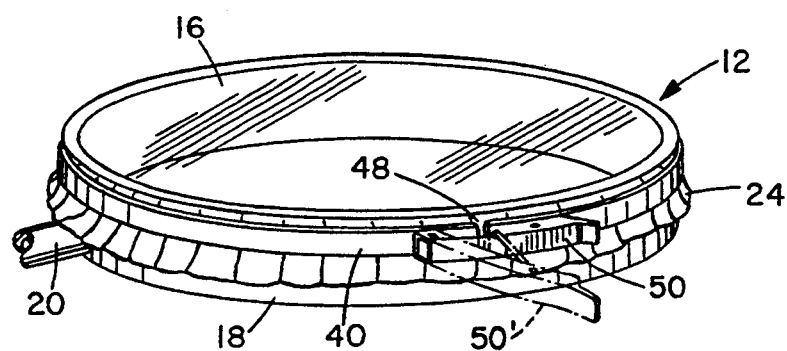
FIG. 7
FIG. 10

POSITIONABLE VIEWING SHIELD WITH DISPOSABLE TRANSPARENT MEDIUM

This is a continuation of co-pending application Ser. No. 07/887,889 filed on May 26, 1992, now abandoned.

BACKGROUND OF THE INVENTION

1. Field of the Invention

The invention herein relates to shield devices to permit a medical practitioner or similar viewer to perform surgery or other tasks while being protected from the spray of body fluids or other liquids.

2. Description of the Prior Art

When a doctor is performing surgery on or examining a patient, it is not uncommon for the patient's body fluids (such as blood, urine or pus) to be suddenly ejected from the patient's body or wound. Since the doctor's face is normally quite close to the surgical incision or wound for the surgery or examination, the doctor gets splattered with that body fluid. In addition to being unpleasant and impeding the doctor's work, such fluids can be dangerous to the doctor, since the body fluid frequently contains infectious organisms which can infect the doctor through contact with his or her eyes, mouth, nostrils or skin. For instance, when a doctor lances a wound, fistula, blister or other lesion, it is common for the liquid matter within to be under pressure and to be ejected in a stream or spray which may carry for a distance of several inches or centimeters.

For protection of doctors against such liquid sprays or streams, there have been a number of prior art devices proposed in the form of air shields, vacuum cabinets, transparent tables and transparent enclosures such as boxes or tents. Such have had only limited success, since they are commonly bulky, often restrict the doctor's movements and commonly require auxiliary equipment to operate, such as vacuum pumps or extensive supporting frameworks.

Most importantly, however, all previous such devices have been useable only with a patient who is at rest and maintaining substantially the same position throughout the medical procedure. Thus such devices have been useable with surgery patients who are comatose while under anesthesia on an operating table or with dental patients who are seated in a dentist's chair. None of the devices, however, is useable with a patient who is active.

In emergency room medical practice, physicians and other emergency room medical personnel must act very rapidly to treat a patient's injury or other acute medical condition. Patients are often in highly agitated states and are only restrained from movement with difficulty. Spurting of blood, pus, urine and similar body fluids is common. There is usually no time for the emergency room staff to assemble complicated equipment such as the prior art devices to provide shielding for the physician and other members of the staff from such fluids, and in any event the violent and frequent movements of many emergency room patients would render such complex and fixed devices unusable.

Further, since the prior art devices have normally been designed to be used in the controlled environment of an operating room, dentist office or the like, such devices have not provided for rapid changing or cleaning of any portion of the device which becomes soiled or contaminated by the patient's body fluids. Commonly the prior art devices have incorporated glass windows supported by complex metal frameworks, which must be carefully disassembled, then cleaned and reassembled for subsequent use. In an emergency room situation, however, it is not uncommon to have a number of patients present all with acute injuries or illnesses who must be attended to in rapid succession. There is no time for the prior art shielding devices to be disassembled, cleaned and reassembled between use for successive patients.

Consequently, it would be highly advantageous to have a viewing device which is readily portable, has a viewing shield which can be quickly and completely changed between patients or even during the course of examination of a single patient, requires little or no supporting structure or auxiliary equipment and which can accommodate reasonable movement by patients.

SUMMARY OF THE INVENTION

In its broadest aspect, the invention is a viewing device which comprises: means for support; a splash guard comprising a hollow frame including a wall forming the perimeter thereof with the area within the perimetrical wall being open to permit visual observation through the open area, the wall having a surface thereon adapted to receive and support a disposable transparent film positioned across the open area; post means for retaining the frame in an elevated position above the means for support; and releasable retaining means cooperating with the wall surface to releasably secure the transparent film positioned under tension across the open area of the frame.

The device will also comprise adjusting means to permit the splash guard to be positioned in varying angular orientations and at varying heights relative to the means for support.

A variety of restraining means to secure the transparent film in position over the open area are suitable, including a resilient band, a toggle strap, a flanged cap and a compression spring.

A variety of films may be used, including films of polyethylene, polypropylene, cellulose acetate, polyester, polyvinylidene chloride and polysulfone.

The device is most valuable in medical emergency room use, but it can also be used in a variety of other settings, including operating rooms, for out-patient examination, in individual physicians' offices, by veterinarians and for inspection or repair of small mechanical products where lubricants, cleaners or other liquids used with such products might be sprayed or splashed into the user's face.

BRIEF DESCRIPTION OF THE DRAWINGS

FIG. 1 is a perspective view of one embodiment of the device of the present invention;

FIG. 2 is a cross-sectional view taken on line 2—2 of FIG. 1 and illustrating a moveable joint within the device;

FIG. 6 is a fragmentary cross-sectional view illustrating an alternative means for securing parts of the device together;

FIG. 7 is a perspective view illustrating another embodiment of the splash guard portion of the device showing an alternative retaining member;

FIG. 8 is a side elevation view showing yet another embodiment of the device which incorporates a clamp to secure the device to a substrate;

FIG. 10 is a view similar to FIG. 4 showing an alternative embodiment of the splash guard portion of the device.

DETAILED DESCRIPTION AND PREFERRED EMBODIMENTS

Figure 3:
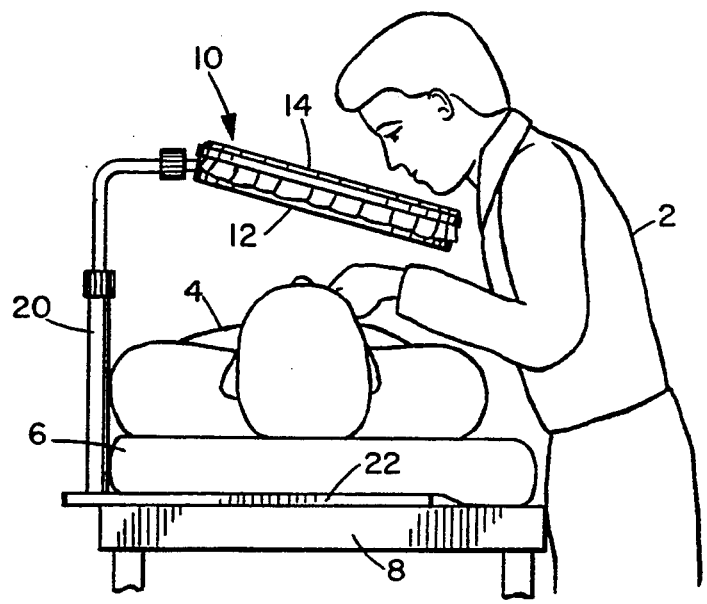
FIG. 3 is a side elevation view of another embodiment of the device showing its manner of use.

The present device and its various embodiments will be best understood by an initial description of its method of use, with reference to FIG. 3. In this figure, a physician 2 is shown treating an emergency patient 4 who is lying on a pad 6 on an examining table or gurney 8. It will be recognized that in an emergency room situation, the patient may be under little or no anesthesia and may be writhing or making other irregular movements. Since the nature and severity of the patient's illness or wound are unknown at the outset of the emergency room examination, the physician has no way to anticipate whether or when he or she will encounter spurting or spraying body fluids from the patient.

The present device (designated generally 10) is therefore conveniently used by the physician as a shield against such fluids. As will be apparent from FIGS. 1 and 3, the device 10 is mounted such that a framework or "splash guard" 12 with an open viewing area 14 is positioned between the physician's face and that portion of the patient's body which is under examination or surgical procedure. The physician looks through a transparent film 16 which covers open area 14 and thus has a clear view of the examination area of the patient's body while being protected by the film from sudden sprays or spurts of the patient's body fluids. As will be described below, film 16 is rapidly and easily removable and disposable, with a new and clean film sheet being quickly mounted, such that the physician retains a clear view of the wound, incision or other area of interest throughout the procedure, while being protected against contact with infectious or noxious fluids.

The major components of the device 10 are illustrated in the FIGURES. The splash guard 12 is formed of a wall 18 which forms a hollow frame with the open area 14 bounded by the wall 18. Commonly the wall 18 is circular, but it may, if desired, be rectangular, square, elliptical, oval, polygonal or other convenient shape. The circular shape is preferred, however, since removal and replacement of the film 16 is most rapid when the retaining device (to be described below) can be placed against the wall or frame 18 without concern about having to align a non-circular wall and cooperating restraining means.

The splash guard 12 is attached to a supporting post 20 which in turn is attached to a base 22. As will be discussed below, the base 22 may itself be part of an examining table or gurney 8. The post 20 allows the splash guard 12 to be elevated at a sufficient distance from the base 22 to provide the physician with adequate room to examine the patient and manipulate surgical tools such as scalpels or probes, as indicated in FIG. 3.

The structure of the splash guard 12 and one preferred means of restraining the film 16 under tension across the open area are illustrated in FIGS. 1 and 2. The film 16 is stretched taut across the open area 14 and is of a size to include a peripheral skirt portion 24 which overlaps and extends downwardly over the outside surface of wall 18 around the perimeter of the wall 18. In the embodiment shown in FIGS. 1 and 2, the restraining means is a resilient band 26, such as a rubber band, which is stretched around the outside of the wall 18 and skirt 24 and allowed to resile into a clamping position over the outside of skirt 24 under sufficient tension to hold the film 16 taut across the open area 14 despite any movements of the device 10 caused by the physician reorienting the device 10 or by the patient's bumping against it. The tension in the band 26 should not be so great, however, that it cannot be quickly removed so that a soiled film sheet 16 can be removed and rapidly replaced by a clean film sheet, which is then again clamped by the band 26.

Figure 4:
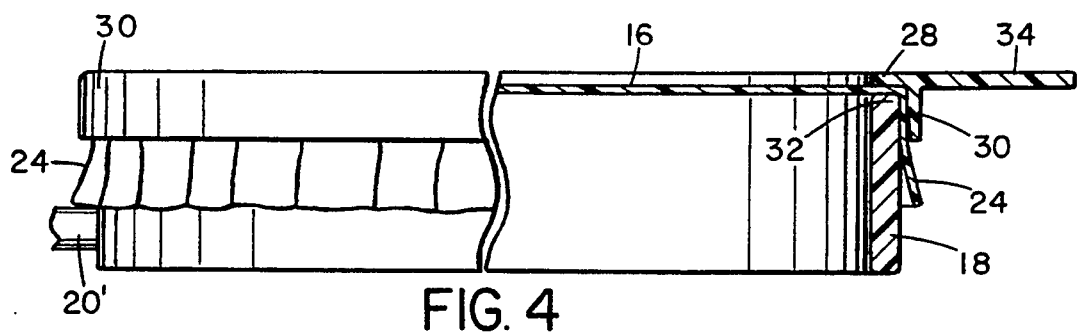
FIG. 4 is a side elevation view, partially cut away, illustrating one embodiment of the splash guard portion of the device.

Other restraining means for securing the film 16 in position are shown in FIGS. 4, 5, 7 and 10. In FIG. 4 an annular lid 28 with a downwardly depending flange 30 fits over the top edge 32 of wall 18 with an interference fit. The skirt portion 24 of film 16 is fitted between the inner surface of flange 30 and the outer surface of wall 18 and the interference fit provides sufficient frictional force to hold the film 16 stretched taut across the open area 14. Conveniently the lid 28 has a gripping handle 34 extending outwardly at one location around the rim so that the lid 28 can be quickly removed and replaced when it is necessary to change film 16, as described above. A similar restraint is shown in FIG. 10 and will be described below.

Figure 5:
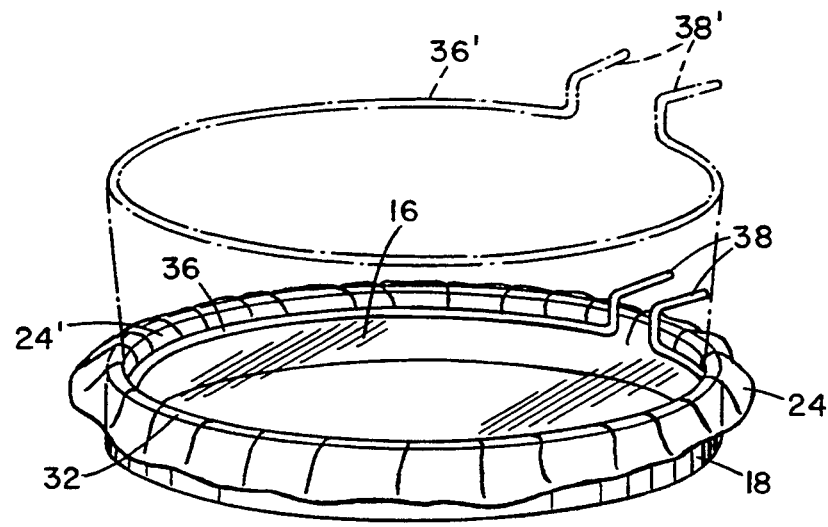
FIG. 5 is a perspective view of another embodiment of the splash guard portion of the device, showing in phantom the use of a spring retaining member.

FIG. 5 illustrates an embodiment in which the restraining means is in the form of a generally circular compression spring 36 which is configured to be compressed to fit within the wall 18 and then expanded to form an interference fit with the inside of wall 18. In this embodiment, the skirt 24 of film 16 includes a portion 24' which extends over the top 32 of wall 18 and downwardly part way inside the wall 18 to provide a bearing surface for the spring 36. Compression of the spring 36 by its end portions 38 allows removal and insertion of the spring as shown in phantom at 36' and 38'.

Yet another embodiment of the splash guard 12 and its retaining means is shown in FIG. 7. In this case the wall 18 is surrounded by a parallel toggle band 40. The toggle band 40 is split at 48 with the two ends of the split band joined by a toggle latch 50 which when closed pulls the two ends together in a clamping relationship against wall 18 with the skirt portion 24 of film 16 restrained between the outer surface of wall 18 and the inner surface of toggle band 40. When the toggle latch 50 is opened as shown in phantom at 50', the two ends of the band 40 are separated effectively expanding the size of toggle band 40 and allowing it to be removed from the periphery of wall 18 to free film 16 for rapid replacement. Once the new film is in place, toggle band 40 can be rapidly replaced in its securing position by the closure of toggle latch 50.

There are a number of ways of mounting the device 10. The simplest mount is that shown in FIG. 1, with the splash guard 12 being attached to post 20 which is secured to a simple flat base 22. Such an embodiment is useful in many situations, but particularly for instance when the patient has suffered an injury to an extremity such as a hand or foot and the physician can position that extremity on the base 22 for examination through the shield 12. Also, as shown in FIG. 3, the base 22 can be slipped under a pad 6 on a gurney or table 8 to hold the device 10 in place.

Figure 9:
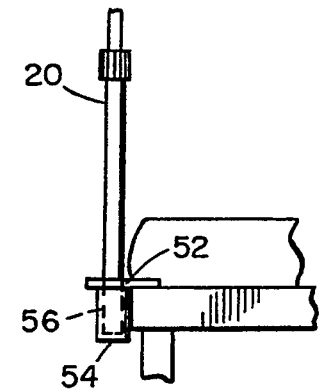
FIG. 9 is a detail side elevation view showing an alternative means for securing the device to a substrate.

Alternatively, it is quite common in emergency room practice for a patient to arrive already on a gurney (when being transported by ambulance from an accident site) or to be placed upon a gurney or examining table 8 immediately upon arrival at the emergency room. It is contemplated that, as shown in FIG. 9, the gurney or examining table 8 could have incorporated into an outer edge or flange 52 of the table surface one or more pockets or recesses 54 which are configured to receive the lower end 56 of post 20. For instance, a typical gurney might have such recesses 54 formed at one foot (30 cm) intervals along its edges to allow the physician to place the device 10 at the most convenient location along the gurney or examining table 8 for efficient examination and treatment of the patient.

Yet another embodiment of mounting means is illustrated in FIG. 6, in which the base 22 has a mounting socket 58 incorporated therein into which the end 56 of post 20 can be placed. Such a configuration would be useful for instance where the base 22 is placed beneath the patient or the pad 6 on which the patient is lying as shown in FIG. 3, as for instance on an ambulance gurney which is not equipped with pockets or recesses 54, and where the physician wishes to be able to move the device 10 to other locations, such as to other base plates 22 which are placed under other portions of the patient's body or the pad 6.

Yet another version of base 22 is shown in FIG. 8, in which the base is at least in part in the form of a clamp 60. The clamp 60 has two jaws 62 and 64 which are urged together by torsion spring 66 and which allow the device to be clamped onto the edge of an examining table or gurney as at 52. The clamp 60 can be released by pressure on the opposite ends 68 of jaws 62 and 64.

Adjustment of the positioning of splash guard 12 can be accomplished in several different ways, some of which allow only for angular adjustment or height adjustment while other permit both simultaneously. In FIGS. 1 and 2, a ball joint 70 is shown which allows angular movement (swivelling) of splash guard 12 with respect to base 22. In a typical configuration, ball 72 is formed on the top end 74 of post 20 and rotates in socket 76 within the threaded sleeve 78. The ball 72 is retained in position by threaded plug 80 which is threaded into sleeve 78 and is secured to wall 18 by bolt 82; plug 80 could also be formed as a projection on one side of wall 18 so that the wall 18 and plug 80 are an one-piece structure and bolt 82 is not needed. Rotation of sleeve 78 causes plug 80 to be moved toward or away from ball 72 so that by loosening the contact between plug 80 and ball 72 the splash guard 12 can be swiveled into different angular positions and then secured in the desired position by once again rotating sleeve 78 to tighten plug 80 against ball 72. Further, plug 80 may have an extended length so that splash guard 12 will be spaced at some distance from ball joint 70.

Also seen in FIG. 1 is telescoping joint 84 which is mounted on the end 86 of the lower portion of 20". Lower portion 20" is hollow and receives in telescoping fashion upper portion 20" of post 20 which is of slightly smaller diameter. There are a variety of known telescoping joint structures, and any of them will be satisfactory as joint 84. Turning the collar operates joint 84 so that the end of top portion 20' which is telescopically received within portion 20" will be released to slide into or out of the interior of portion of 20" or will be restrained at a fixed position by frictional engagement between the two post portions 20' and 20".

It will of course be evident that a given post 20 can have either or both of joints 70 and 84 but may also have only one, so that the splash guard 12 may be swiveled but not raised or lowered, or vice versa.

Another configuration that allows motion of the splash guard 12 is shown in FIG. 8, in which joints 70 and 84 are eliminated and an upper section of post 20 is replaced by flexible extension or gooseneck 88, which is commonly in the form of a tightly wound spring. Gooseneck 88 has sufficient stiffness to remain in any orientation in which it is placed, but yet sufficient flexibility to allow it to be turned or twisted to align and orient the splash guard 12 at any height, position or angle that the physician wishes. The gooseneck 88 is secured to post 20 and splash guard 22 by fixed joints 90 and 92 respectively.

It is also possible to use some of these structures together. For instance, one could have a gooseneck 88 in combination with a ball joint 70, such that the segment 74 projecting from ball 72 is fitted into joint 92. Other similar combinations of structures will be evident to those skilled in the art.

Any type of transparent film or sheet material can be used as film 16. The film may be thick and have sufficient rigidity of its own to be placed (as shown in FIG. 10) across the top of open space 14 and rest on the top edge 32 of wall 18, as indicated at 16'. A clamp such as cap 28 with its flange 30 will then be placed over the top to secure the stiff film 16' in place. This configuration is less preferred in an emergency room setting, however, since it requires that the emergency room keep on hand a supply of film sheets 16' of the exact size for the specific diameter of the splash guard 12 of the device 10 being used.

More preferably, however, the film 16 as noted above is a flexible film sheet with a diameter or size sufficiently large to cover the open space 14 and include a peripheral extended skirt 24. The film can be stored in a large enough size that a variety of different devices can be accommodated, including ones which are not necessarily circular. Alternatively, the film can be stored in roll form and cut off in lengths long enough to provide the adequate viewing area size plus the skirt length. Containers with a built-in cutting edge can be provided in the same manner that foil and plastic films are provided in cutting boxes for kitchen use.

Any of a wide variety of transparent plastic or polymeric films can be used, including but not limited to films of polyethylene, polypropylene, cellulose acetate, polyester (such as the "Mylar ®" polyester films), polyvinylidene chloride (such as the saran films), polysulfone and the like. After use they may simply be disposed of the same manner as other medical waste such as dressings and surgical drapes.

The above description has been exemplified in the context of medical emergency room use, since such use has unique requirements which clearly illustrate the flexibility and rapid film replacement characteristics of the present invention which set it apart from all prior art devices. It will be evident to those skilled in the art, however, that the device can be used in a variety of other settings, including some of those to which prior art devices have previously been directed. It may of course be used in an operating room setting or for outpatient examination, as well as in an individual physician's office for examination of his or her patients. It can be used by veterinarians during surgery on or examination of animals, either in a emergency room or regular animal surgery setting. It can also be used in non-medical settings, as for instance for inspection or repair of small mechanical products such as appliances, models, timepieces and similar objects, where lubricants, cleaners or other liquids used with such products might be sprayed or splashed into the user's face.

It will also be evident that there are numerous embodiments of this invention which, while not expressly set forth above, are clearly within the scope and spirit of the invention. Consequently, the above description is intended to be exemplary only, and the scope of the invention is to be limited solely by the appended claims.

I claim:

1. A viewing device to enable a medical attendant to view an area of a patient's body while said attendant is being protected from contact with fluid emissions from said area comprising:
   means for supporting said device in a position proximate to said attendant;
   a splash guard comprising a hollow frame including a wall having a top edge and forming a perimeter thereof with the area within said perimetrical wall being open to permit visual observation through said open area, said wall having a surface thereon receiving and supporting a sheet of flexible, disposable transparent film positioned across said open area;
   post means for retaining said splash guard in an elevated position above said support means;
   positioning means for orienting said splash guard at a plurality of distances from and a plurality of angular orientations relative to said means for support; and
   releasable retaining means cooperating with and connected against said wall surface immediately adjacent said top edge releasably securing said transparent sheet between said retaining means and said wall surface whereby said sheet of transparent film is positioned under tension across said open area of said frame.

2. A device as in claim 1, further comprising:
   a ball-and-socket joint member joining said post means and said splash guard.

3. A device as in claim 1; further comprising:
   two segments and a telescoping joint member joining said segments and permitting one segment to telescope within the other segment.

4. A device as in claim 1 wherein said positioning means comprises a gooseneck.

5. A device as in claim 1 wherein said support means comprises a clamp connected at a lower end of said post means.

6. A device as in claim 1 wherein said support means comprises a recess incorporated in a substrate and an end of said post means distal from said splash guard is configured to be seated and releasably secured within said recess.

7. A device as in claim 1 wherein said frame has a generally annular shape.

8. A device as in claim 1 wherein said wall and said retaining means are nested and parallel, and have a releasable interference fit when nested sufficient to accommodate and retain a perimetrical portion of said sheet of transparent film therebetween when said sheet of transparent film is positioned over said open area.

9. A device as in claim 8 wherein said retaining means comprises two abutting segments and locking means to move said segments relative to each other, such that said retaining means can be moved into and out of nesting relationship with said wall.

10. A device as in claim 9 wherein said locking means comprises a toggle.

11. A device as in claim 8 wherein said retaining means comprises a resilient member which is removably nested within said wall.

12. A device as in claim 11 wherein said resilient member comprises a spring.

13. A device as in claim 8 wherein said retaining means comprises a resilient band.

14. A device as in claim 8 wherein said retaining means comprises a flange member removably disposed surrounding and parallel to said wall.

15. A viewing device for enabling a medical attendant positioned adjacent one side of a substrate to view an area of a patient's body being supported atop the substrate, the head and upper torso of said attendant being protected by said device from contact with fluid and solid emissions from said area, comprising said substrate:
   a single, elongated post having an upper and a lower end;
   a means for supporting said lower end whereby said post is in an upright orientation extending upwardly from the substrate, said support means releasably engagable along a side opposite said one side of the substrate;
   a splash guard comprising a frame including a continuous wall having a top edge and forming a perimeter thereof with an area within said perimeter being open to permit visual observation through said open area;
   a positioning means interconnected between said upper end and a point along said frame nearer to said opposite side than said one side of the substrate for retaining said splash guard in an elevated position above the substrate at a plurality of distances from and a plurality of angular orientations relative to the substrate;
   a sheet of disposable, flexible transparent film positionable across said open area against said top edge;
   releasable retaining means connected against said wall surface immediately adjacent and below said top edge releasably securing said transparent sheet between said retaining means and said wall surface whereby said sheet of transparent film is positioned under tension across said open area.

16. A method of protecting a head and upper torso of a medical attendant positioned along one side of a substrate from contact with fluid and solid emissions from an area of a patient's body being supported atop the substrate while said area is being viewed by said attendant comprising the steps of:
   A. connecting a viewing device to a side opposite said one side of the substrate;
   said viewing device comprising:
      a single, elongated post having an upper and a lower end;
      a means for supporting said lower end whereby said post is in an upright orientation extending upwardly from the substrate, said support means releasably engagable along said opposite side of the substrate;

a splash guard comprising a frame including a continuous wall having a top edge and forming a perimeter thereof with an area within said perimeter being open to permit visual observation through said open area;

a positioning means interconnected between said upper end and a point along said frame nearer to said opposite side than said one side of the substrate for retaining said splash guard in an elevated position above the substrate at a plurality of distances from and a plurality of angular orientations relative to the substrate;

a sheet of disposable, flexible transparent film across said open area against said top edge;

releasable retaining means connected against said wall surface immediately adjacent and below said top edge releasably securing said transparent sheet between said retaining means and said wall surface whereby said sheet of transparent film is positioned under tension across said open area;

B. elevating and orienting said splash guard as desired for optimal viewing and protection from said area by said attendant;

C. replacing said sheet of transparent film as required.

* * * * *

UNITED STATES PATENT AND TRADEMARK OFFICE
CERTIFICATE OF CORRECTION

PATENT NO. : 5,360,018
DATED : November 1, 1994
INVENTOR(S) : Sutton Chen

It is certified that error appears in the above-identified patent and that said Letters Patent is hereby corrected as shown below:

Column 8, Lines 26 and 27, replace "solid emissions from said area, comprising said substrate:" with -- solid emissions from said area, comprising:
    said substrate; --

Signed and Sealed this

Third Day of January, 1995

Attest:

BRUCE LEHMAN

Attesting Officer

Commissioner of Patents and Trademarks